United States Patent
Ueda (10) Patent No.: US 10,598,912 B2
(45) Date of Patent: Mar. 24, 2020

(54) OBJECTIVE OPTICAL SYSTEM FOR ATR MEASUREMENT

(71) Applicant: Shimadzu Corporation, Kyoto (JP)

(72) Inventor: Atsushi Ueda, Kyoto (JP)

(73) Assignee: Shimadzu Corporation, Nishinokyo-Kuwabaracho, Nakagyo-ku, Kyoto-shi, Kyoto (JP)

( * ) Notice: Subject to any disclaimer, the term of this patent is extended or adjusted under 35 U.S.C. 154(b) by 162 days.

(21) Appl. No.: 15/539,706

(22) PCT Filed: Jan. 5, 2015

(86) PCT No.: PCT/JP2015/050051
§ 371 (c)(1),
(2) Date: Jun. 26, 2017

(87) PCT Pub. No.: WO2016/110935
PCT Pub. Date: Jul. 14, 2016

(65) Prior Publication Data
US 2017/0371139 A1    Dec. 28, 2017

(51) Int. Cl.
*G02B 21/04*     (2006.01)
*G01N 21/552*    (2014.01)
(Continued)

(52) U.S. Cl.
CPC .............. *G02B 21/04* (2013.01); *G01N 21/35* (2013.01); *G01N 21/3577* (2013.01);
(Continued)

(58) Field of Classification Search
CPC .. G01N 21/35; G01N 21/3577; G01N 21/552; G01N 2201/0636;
(Continued)

(56) References Cited

U.S. PATENT DOCUMENTS

| | | | |
|---|---|---|---|
| 5,347,364 A | 9/1994 | Kawasaki et al. | |
| 2013/0278922 A1* | 10/2013 | Gelernt | G02B 21/16 356/51 |

FOREIGN PATENT DOCUMENTS

| | | |
|---|---|---|
| JP | H06-003262 | 1/1994 |
| JP | H07-012717 | 1/1995 |

(Continued)

OTHER PUBLICATIONS

International Search Report for PCT/JP2015/050051 dated Mar. 17, 2017.
(Continued)

*Primary Examiner* — Joseph P Martinez
*Assistant Examiner* — Vipin Patel
(74) *Attorney, Agent, or Firm* — Muir Patent Law, PLLC (57) ABSTRACT

An objective optical system includes a convex secondary mirror configured to reflect a measurement light irradiated from an infrared microscope, a concave primary mirror configured to reflect the measurement light reflected by the secondary mirror, a prism to which the measurement light reflected by the primary mirror is irradiated, and a light shielding means provided on an optical path of the measurement light between the primary mirror and the prism to shield a part of the light beam of the measurement light.

5 Claims, 9 Drawing Sheets

(51) Int. Cl.
*G01N 21/3577* (2014.01)
*G02B 21/26* (2006.01)
*G01N 21/35* (2014.01)
*G02B 7/18* (2006.01)

(52) U.S. Cl.
CPC .......... *G01N 21/552* (2013.01); *G02B 21/26* (2013.01); *G01N 2201/064* (2013.01); *G01N 2201/0636* (2013.01); *G01N 2201/0638* (2013.01); *G02B 7/1805* (2013.01)

(58) Field of Classification Search
CPC ..... G01N 2201/0638; G01N 2201/064; G01N 2201/04; G01N 2201/26; G02B 7/1805
See application file for complete search history.

(56) References Cited

FOREIGN PATENT DOCUMENTS

| | | |
|---|---|---|
| JP | H11-044636 | 2/1999 |
| JP | 3184487 B2 | 4/2001 |

OTHER PUBLICATIONS

Partial Supplementary European Search Report dated Dec. 22, 2017 for the corresponding European Patent Application No. 15876813.5.
English Translation of the Written Opinion of the International Search Authority re PCT/JP2015/050051 dated May 2, 2017.

\* cited by examiner

OBJECTIVE OPTICAL SYSTEM FOR ATR MEASUREMENT

TECHNICAL FIELD

The present invention relates to an objective optical system used for a sample surface analysis by an attenuated total reflection method using an infrared microscope.

BACKGROUND TECHNIQUE

Figure 13A:
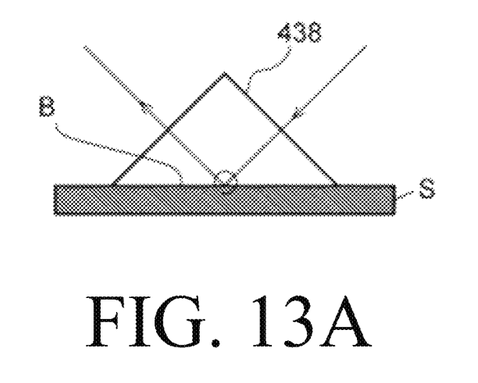
FIG. 13A shows a state in which infrared light is totally reflected by a boundary surface between a sample and an ATR prism.
Figure 13B:
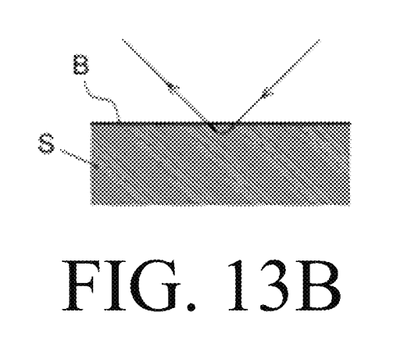
FIG. 13B shows an enlargement of a circled area in FIG. 13A.

As one of surface analysis methods performed by an infrared microscope, there is an attenuated total reflection (ATR) method (hereinafter, a measurement by the ATR method is referred to as "ATR measurement). In the ATR measurement, as shown in FIG. 13A, a sample S is press-contacted to a prism (ATR prism) 438 having a higher refractive index than that of the sample S, and infrared light is irradiated on the surface of the sample S at an incident angle equal to or more than the total reflection critical angle. Then, after incident on the ATR prism 438, the infrared light is totally reflected by the boundary surface B between the ATR prism 438 and the sample S. At the time of the total reflection, as shown in FIG. 13B, the infrared light slightly (a fraction of the wavelength of the measured infrared light) penetrates toward the sample S side beyond the boundary surface B and receives inherent absorption by the surface portion of the sample S. As described above, in the ATR measurement, the sample surface analysis can be performed by analyzing the absorption spectrum of the infrared light slightly penetrated into the sample surface and then reflected from the sample.

Figure 14:
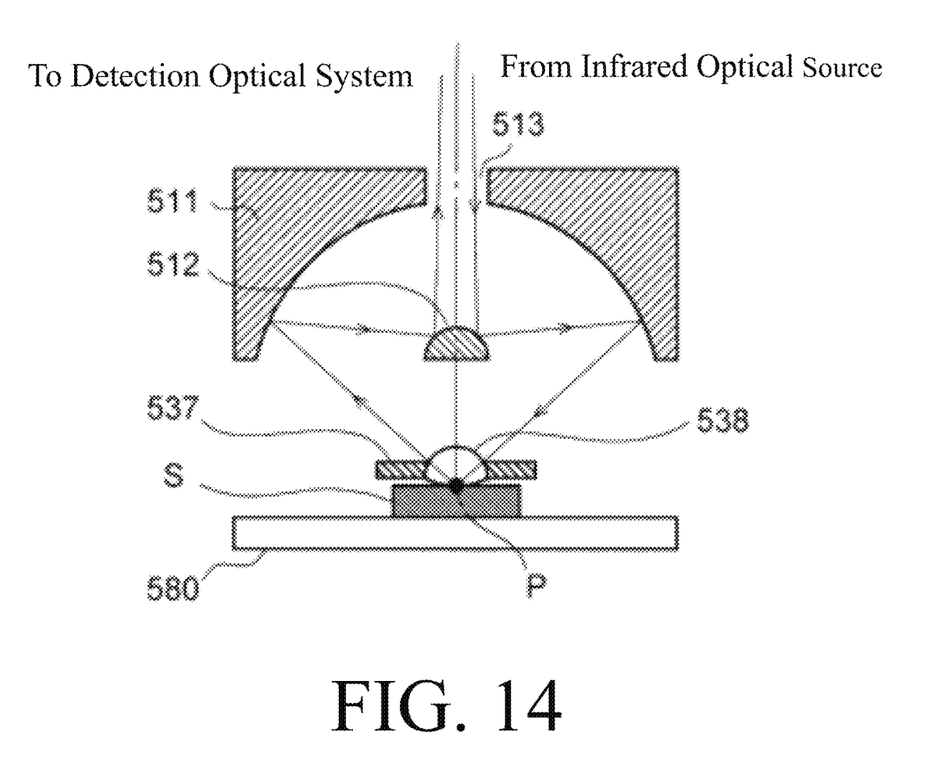
FIG. 14 is a schematic configuration diagram of a conventional infrared microscope system.

FIG. 14 is a diagram showing a configuration of a general objective optical system used in an infrared microscope in recent years. The illustrated objective optical system includes Cassegrain mirrors (also called Schwarzschild type reflection objective mirrors), an approximately hemispherical ATR prism 538, and a prism holder 537 for holding the ATR prism 538. The Cassegrain mirrors are provided with a concave primary mirror 511 having an opening 513 in the center and a convex secondary mirror 512 arranged immediately below the opening 513. The primary mirror 511 is fixed with the concave surface facing downward, and the secondary mirror 512 is fixed with the convex surface facing upward. The diameter of the ATR prism 538 is about several millimeters. Here, the bottom surface of the ATR prism 538 is a perfect plane or a spherical shape bulging slightly downward, and the region where the ATR prism 538 and the sample S are in contact is a small region of about several tens to several hundreds of micrometers in diameter. Hereinafter, this small region will be referred to as "contact point P" between the prism and the sample. In addition to the above, an infrared light source, a visible light source, a detection optical system for detecting infrared light, a visual optical system for visually observing a sample using visible light, a sample stage 580 for arranged a sample S, etc., are included as constituent elements of the infrared microscope.

The light (measurement light) from the infrared light source is incident on the secondary mirror 512 from above the objective optical system via the opening 513, and is reflected by the convex surface of the secondary mirror 512 and incident on the primary mirror 511. The measurement light reflected and condensed by the concave surface of the primary mirror 511 is incident on the ATR prism 538 arranged at the focal point of the primary mirror 511 and irradiated to the contact point P. The reflected infrared light from the sample S is incident on a detection optical system of the infrared microscope through the primary mirror 511 and the secondary mirror 512 and detected.

As described above, the ATR method is an analysis method in which a total reflected light absorbed and attenuated in the process that the measurement light slightly penetrated the sample surface passes through the sample surface layer is measured to obtain an absorption spectrum of the sample surface layer. The penetration depth of the measurement light at this time depends on the refractive index "n" of the ATR prism and the incident angle θ of the light to the sample. Among these, in order to change the refractive index "n", it is necessary to prepare a plurality of ATR prisms of different materials. However, an ATR prism is relatively expensive, resulting in an increased cost for the ATR measurement.

Also, in order to obtain high optical throughput by the ATR measurement, it is necessary to widen the incident angle range of the light incident on the sample from the Cassegrain mirror. When the minimum incident angle is decreased to increase the solid angle of the opening of the reflection objective mirror, the minimum incident angle approaches the critical angle. Therefore, due to the influence of anomalous dispersion of refractive index "n", there is a problem that shape changes of the absorption peak (differential shape formation, low wave number peak intensity becomes relatively large, shift to a low wave number side, etc.) occurs easily. On the other hand, in order to suppress the influence of anomalous dispersion of refractive index "n", it is necessary to increase the minimum incident angle of the light incident on the sample from the Cassegrain mirror. However, in that case, there is a problem that the solid angle of the opening of the Cassegrain mirror decreases and therefore the optical throughput decreases. As described above, there is a trade-off relationship between the improvement of optical throughput and the reduction of anomalous dispersion, and in a conventional objective optical system, the angle range of incident light is fixed according to the measurement purpose and the design intention. Therefore, when performing a measurement which prioritizes the optical throughput and a measurement which prioritizes mitigation of the anomalous dispersion of refractive index "n", respectively, it is necessary to select one of a plurality of objective optical systems.

Figure 15A:
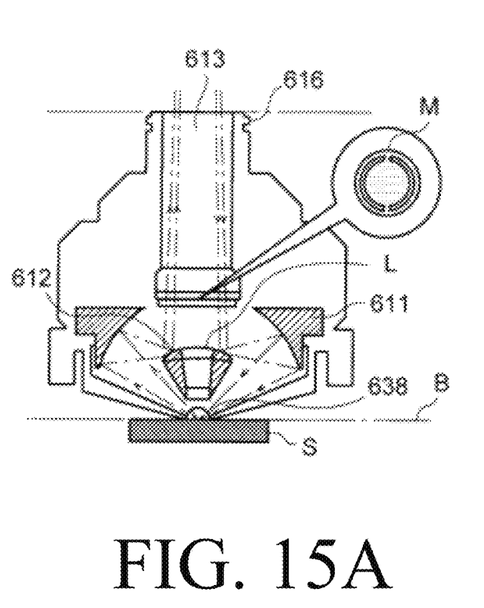
FIG. 15A is a schematic diagram of the former.

In order to solve these problems, Patent Document 1 describes an objective optical system that can obtain different absorption spectra different in penetration depth by using a single ATR prism by changing the incident angle range of light to the sample. As shown in FIG. 15A, in the objective optical system, a light shielding mask M having an arcuate opening is arranged above the secondary mirror 612 so that a part of the measurement light incident on the secondary mirror 612 from the infrared light source can be shielded. A plurality of light shielding masks M different in shape and size of the openings are prepared. By switching light shielding masks to be placed on the optical path of the measurement light by a predetermined slide mechanism, it is possible to change the incident angle range of the light incident on the sample S via the secondary mirror 612, the primary mirror 611, and the ATR prism 638.

PRIOR ART

Patent Document

Patent Document 1: Japanese Unexamined Patent Application Publication No. 11-044636

SUMMARY OF THE INVENTION

Figure 15B:
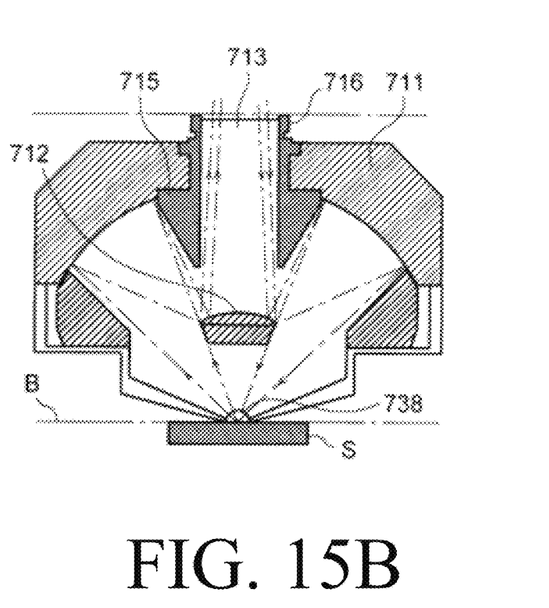
FIG. 15B is a schematic diagram of the latter.

In the objective optical system described in Patent Document 1 described above, the light shielding mask M and the sliding mechanism are arranged at predetermined positions of the objective optical system. Specifically, the light shielding mask M and the sliding mechanism are arranged at any position below the mounting portion 616 for mounting the objective optical system to the revolver of the infrared microscope and above the region in which a Cassegrain mirror composed of a primary mirror 611 and a secondary mirror 612 are accommodated. However, in recent objective optical systems, as shown in FIG. 15B, the distance from this mounting portion (716 in FIG. 15B) to the Cassegrain mirror (711 and 712 in FIG. 15B) is shorter than that in the prior art. This is due to the difference in imaging magnification between the conventional objective optical system and the recent objective optical system.

When the distance from the boundary surface B of the sample S and the ATR prism to the Cassegrain mirror is short, the imaging magnification becomes high. On the other hand, when the distance is long, the imaging magnification becomes low. In the conventional objective optical system as shown in FIG. 15A, when positioning a sample S, etc., a relatively high magnification (about 30 times) was required because the sample surface was observed with a naked eye using a visual optical system including an objective lens L made of glass, etc. However, when the imaging magnification is increased, there is a problem that the observable area (visual field) is narrowed, causing a difficulty in searching the measurement target area on the sample surface. For this reason, in recent years, it is a mainstream to use a combination of an objective optical system of a relatively low imaging magnification of about 15 times and a visual optical system equipped with a digital camera, such as, e.g., a CCD camera and a CMOS camera. In this case, the image of the sample surface photographed with the digital camera of the visual optical system can be displayed on a monitor or the like of a personal computer and observed while enlarging it with a digital zoom, etc., as necessary.

That is, in an objective optical system for an ATR measurement of recent years (FIG. 15B), for the purpose of lowering the imaging magnification more than before, the distance from the boundary surface B to the Cassegrain mirrors 711 and 712 is designed to be long. On the other hand, the distance from the Cassegrain mirrors 711 and 712 to the mounting portion 716 is short. Furthermore, in an objective optical system of recent years, a baffle 715 for reducing stray light is provided on the inner periphery of the opening provided in the primary mirror 711. From these facts, in an objective optical system of recent years, there is no enough space above the Cassegrain mirror, and therefore it is difficult to arrange a light shielding mask M and a slide mechanism above the secondary mirror 612 as in the objective optical system (FIG. 15A) described in Patent Document 1. Provided that a hole is formed in the primary mirror, it is possible to arrange a light shielding mask, etc., above the secondary mirror. In such a case, however, intrusion of ambient light into the Cassegrain mirror becomes a problem.

Further, since the light beam of the measurement light above the secondary mirror is relatively thin, in order to achieve the desired incident angle θ, it is necessary to process the opening to be formed in the light shielding mask M with high precision. In addition, the light shielding mask M is required to be configured such that the light shielding mask M can be strictly positioned on the optical path of the measurement light, which results in an increased manufacturing cost.

According to disclosed embodiments of the present invention, an objective optical system for an ATR measurement is provided that is capable of achieving both of a measurement which provides optical throughput in a single objective optical system and a measurement which mitigates influence due to anomalous dispersion of refractive index, where a penetration depth of measurement light to a sample may be easily adjusted, and where the system may be manufactured at a relatively low cost.

According to some disclosed example embodiments, an objective optical system used for sample surface analysis by an attenuated total reflectance method by being attached to an infrared microscope, comprises a) a convex secondary mirror configured to reflect measurement light irradiated from the infrared microscope;

b) a concave primary mirror configured to reflect the measurement light reflected by the secondary mirror;

c) a prism to which the measurement light reflected by the primary mirror is irradiated, and d) light shielding means configured to shield a part of a light beam of the measurement light on an optical path of the measurement light between the primary mirror and the prism.

With this configuration, since it is configured to shield a part of the light beam of the measurement light between the primary mirror and the prism, even in cases where there is no enough space on the front side (above) of the secondary mirror like the above-described objective optical system of recent years, the incident angle range of the measurement light to the sample can be adjusted. Therefore, even in an objective optical system designed to obtain large optical throughput by increasing the solid angle of the opening of the Cassegrain mirror, by changing the minimum incident angle using the light shielding means, it is possible to reduce the influence of anomalous dispersion due to incident light near the critical angle. In addition, by using the light shielding means, it is also possible to easily adjust the penetration depth of the measurement light to the sample.

Further, on the optical path between the primary mirror and the prism, the light beam of the measurement light is relatively thick (compared with the front side of the secondary mirror), and the incident angle will not fluctuate greatly due to the slight difference in shape, size, and position of the light shielding mask like the objective optical system of recent years. As a result, the objective optical system according to the present invention has an advantage that it can be produced relatively inexpensively since high precision is not required for producing and positioning the light shielding means.

Some exemplary disclosed embodiments also comprise e) a housing which accommodates the primary mirror and the secondary mirror; and f) a prism holder which holds the prism and is detachably attached to a lower portion of the housing, wherein the light shielding means is a light shielding mask mounted above the prism above the prism holder.

With such a configuration, by attaching the light shielding mask to the prism holder or removing the light shielding mask from the prism holder, the amount of the light beam shielded by the light shielding means (light shielding amount) can be easily changed. As a result, the incident angle range of the measurement light to the sample can be easily adjusted, which makes it possible to easily switch between the measurement which prioritizes optical throughput and the measurement which prioritizes mitigation of anomalous dispersion in a single objective optical system. It is also possible to easily obtain a plurality of absorption spectra measured at different penetration depths by adjusting the incidence angle range.

Further, it may be configured such that a prism holder to which a light shielding mask is attached and a prism holder to which a light shielding mask is not attached are prepared in advance and the light shielding amount can be changed by appropriately exchanging a prism holder to be attached to the housing.

Alternatively, it may be configured such that the light shielding amount can be changed by preparing a plurality of light shielding masks having different shapes and sizes in advance, and appropriately replacing the light shielding mask to be attached to the prism holder, or fixing a plurality of light shielding masks to different prism holders and appropriately exchanging a prism holder to be attached to the housing.

The objective optical system may be configured such that
the primary mirror is provided with an opening for introducing measurement light and arranged with the concave surface facing downward,
the secondary mirror is arranged below the primary mirror with the convex surface facing upward,
it is configured such that the light beam of the measurement light incident from above the primary mirror through the opening is reflected by the convex surface of the secondary mirror and the reflected light is reflected again by the concave surface of the primary mirror to be condensed on a single point below the secondary mirror, and
the light shielding means is a light shielding mask arranged horizontally below the secondary mirror in a vertically movable manner.

According to this configuration, by vertically moving the light shielding mask, it is possible to easily change the light shielding amount of the measurement light by the light shielding mask and adjust the incident angle range of the measurement light to the sample. Therefore, similarly to the above, with a single objective optical system, it becomes possible to easily switch between the measurements which prioritizes optical throughput and the measurement which prioritizes mitigation of anomalous dispersion or easily acquire multiple absorption spectra measured at different penetration depths.

Alternatively, the objective optical system may be configured such that
the primary mirror is provided with an opening for introducing measurement light and arranged with the concave surface facing downward,
the secondary mirror is arranged below the primary mirror with the convex surface facing upward,
it is configured such that the light beam of the measurement light incident from above the primary mirror through the opening is reflected by the convex surface of the secondary mirror and the reflected light is reflected again by the concave surface of the primary mirror to be condensed on a single point below the secondary mirror,
the light shielding means is a light shielding mask arranged below the secondary mirror, and
the light shielding mask is configured to be rotatable about an axis extending parallel to the light shielding mask in a horizontal direction.

According to such a configuration, by rotating the light shielding mask around the axis, it is possible to easily change the light shielding amount of the measurement light by the light shielding mask and adjust the incident angle range of the measurement light to the sample. Therefore, similarly to the above, with a single objective optical system, it becomes possible to easily switch between the measurements which prioritizes optical throughput and the measurement which prioritizes mitigation of anomalous dispersion or easily acquire multiple absorption spectra measured at different penetration depths.

Accordingly, with a single objective optical system, it becomes possible to provide an objective optical system for an ATR measurement capable of easily switching between the measurements which prioritizes optical throughput and the measurement which prioritizes mitigation of anomalous dispersion or easily acquiring multiple absorption spectra measured at different penetration depths, which may be produced at a relatively low cost as a single objective optical system.

BRIEF DESCRIPTION OF THE DRAWINGS

FIGS. 7A and 7B are plan views of a light shielding mask in the aforementioned embodiment.

FIGS. 8A to 8F are diagrams showing another configuration example of a light shielding means of the aforementioned embodiment. FIG. 8B is a front view thereof.

FIGS. 13A and 13B are schematic diagrams for explaining a principle of an ATR method.

FIGS. 15A and 15B are diagrams for comparing an objective optical system described in Patent Document 1 with an objective optical system of recent years.

EMBODIMENT FOR CARRYING OUT THE INVENTION

Hereinafter, embodiments for carrying out the present invention will be described with reference to the drawings.

Embodiment 1

Figure 1:
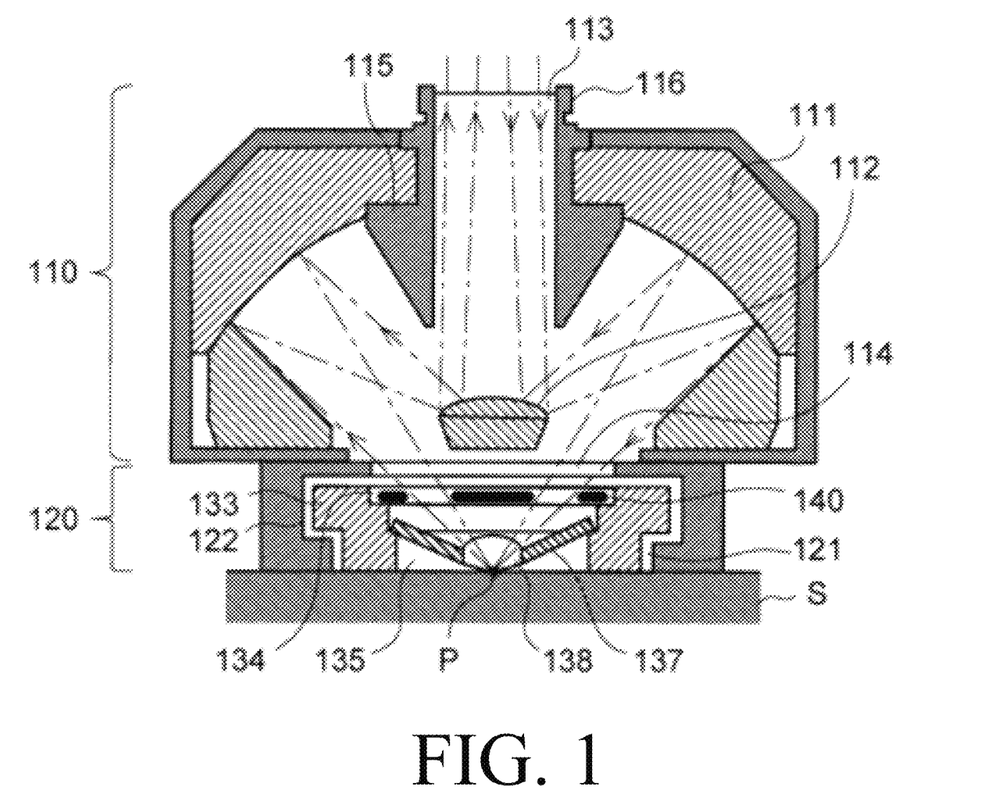
FIG. 1 is a vertical cross-sectional view of an objective optical system according to a first embodiment of the present invention.

FIG. 1 is a vertical cross-sectional view of an objective optical system according to a first embodiment of the present invention. This objective optical system is used in a state of being attached to a revolver of an infrared microscope, and is provided with a Cassegrain mirror accommodation portion 110 accommodating Cassegrain mirrors and a prism accommodation portion 120 accommodating an approximately hemispherical ATR prism 138.

The Cassegrain mirror accommodation portion 110 is provided at its upper end with a mounting portion 116 to be mounted to a revolver of an infrared microscope. In the Cassegrain mirror accommodation portion 110, a concave primary mirror 111 and a convex secondary mirror 112, which constitute Cassegrain mirrors, are accommodated. The concave surface of the primary mirror 111 and the convex surface of the secondary mirror 112 each have a circular outer shape when viewed from above. The primary mirror 111 has at its center portion an opening for introducing light, and is held by the Cassegrain mirror accommodation portion 110 with its concave surface facing downward. The secondary mirror 112 is arranged below the primary mirror 111 with the convex surface facing upward. At the upper and lower portions of the Cassegrain mirror accommodation portion 110, an upper opening 113 and a lower opening 114 for passing light are provided. At the inner periphery of the upper opening 113, a baffle 115 which is a light shielding member for reducing stray light is arranged.

The prism accommodation portion 120 is a columnar member used by being attached to the lower portion of the Cassegrain mirror accommodation portion 110 and has a plate accommodation portion 121 for accommodating a slide plate 130 holding the ATR prism 138.

Figure 2:
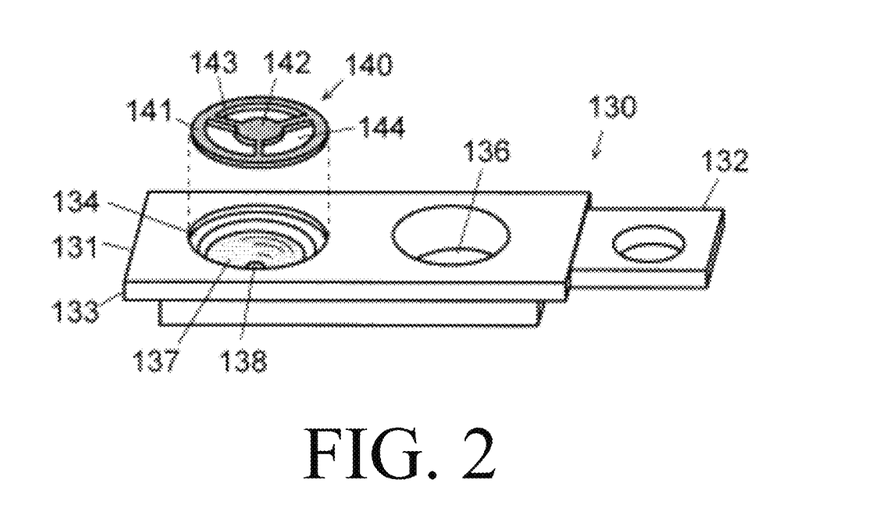
FIG. 2 is a perspective view of a slide plate and a light shielding mask in the aforementioned embodiment.

FIG. 2 shows a configuration of the slide plate 130. The slide plate 130 has a main body portion 131 which is a rectangular plate member and a gripping portion 132 attached to the short side of the main body portion 131. On the side surface of the main body portion 131, a convex portion 133 is formed along the longitudinal direction. By engaging the convex portion 133 with the groove-like recesses 122 provided on the inner surface of the plate accommodation portion 121, the slide plate 130 can be held slidably in the prism accommodation portion 120.

On the upper surface of the main body portion 131 of the slide plate 130, a mask accommodation portion 134, which is a circular recess, is formed. At the center of the mask accommodation portion 134, an opening 135 for a prism, which is a circular through-hole having a diameter smaller than that of the mask accommodation portion 134, is provided. Further, next to the mask accommodation portion 134 and the opening 135 for a prism, an opening 136 for visual observation, which is a through-hole having substantially the same diameter as that of the opening 135 for a prism, is provided. In the opening 135 for a prism, a prism holder 137 having a mortar-like shape is accommodated. In this prism holder 137, an ATR prism 138 is fitted in the opening provided in the center thereof.

In the mask accommodation portion 134, a light shielding mask 140 which is a characteristic element of the present invention is accommodated. The light shielding mask 140 is made of a thin circular plate having light shielding properties, and is equipped with an annular frame part 141, a circular light shielding portion 142 positioned in the center of the frame part 141, and connecting portions 143 for connecting the frame part 141 and the light shielding portion 142 to each other. The outer diameter of the light shielding portion 142 is smaller than the inner diameter of the frame part 141. As a result, an arc shaped slit 144 is formed between the outer periphery of the light shielding portion 142 and the inner periphery of the frame part 141.

Note that the light shielding mask 140 may be fixed to the mask accommodation portion 134 of the slide plate 130 with an adhesive or the like. Alternatively, it may be simply placed in the mask accommodation portion 134. In cases where the light shielding mask 140 is not fixed to the slide plate 130, there is an advantage that the user can easily attach and detach the light shielding mask 140 to the slide plate 130 as needed. On the other hand, in cases where the light shielding mask 140 is fixed to the slide plate 130, there is an advantage that possible loss of the light shielding mask 140, which is a small part, can be prevented. In this case, it is preferable that, apart from the slide plate 130 to which the light shielding mask 140 is fixed, a slide plate with no light shielding mask 140 is prepared so that both the slide plates can be selectively used as necessary.

When performing an analysis by an ATR method using the objective optical system having the above-described configuration, initially, in a state in which the objective optical system is attached to an infrared microscope, a user places a sample S on the sample stage of the infrared microscope. Then, the slide plate 130 is slid in the horizontal direction so that the opening 136 for visual observation is positioned immediately below the lower opening 114 of the Cassegrain mirror accommodation portion 110. In this state, when light (visible light) from a visible light source provided in the infrared microscope is irradiated to the Cassegrain mirror through the upper opening 113, the visible light is reflected by the secondary mirror 112 and the primary mirror 111 and irradiated to the sample S. The light reflected on the surface of sample S is incident to the infrared microscope through the upper opening 113 of the Cassegrain mirror accommodation portion 110 via the primary mirror 111 and the secondary mirror 112. The image obtained by this incident light is photographed by a CCD camera or the like provided in the visual optical system of the infrared microscope and displayed on a PC monitor or the like. The user adjusts the position of the sample S by moving the sample stage while visually observing the image displayed on the monitor or the like and positions the region (measurement point) to be measured on the surface of the sample S at the focal point of the primary mirror 111.

When the position of the sample S is thus determined, the user again slides the slide plate 130 in the horizontal direction. This time, the opening 135 for a prism is positioned immediately below the lower opening 114 of the Cassegrain mirror accommodation portion 110. As a result, since it becomes a state in which the ATR prism 138 is placed above the measurement point of the sample S, the sample stage is further raised so that the sample S is press-contacted to the bottom surface of the ATR prism 138. In this state, when the light (infrared light) from the infrared light source provided in the infrared microscope is irradiated to the Cassegrain mirror through the upper opening 113, the infrared light (measurement light) is reflected by the secondary mirror 112 and the primary mirror 111 and then incident to the opening 135 for a prism. At this time, when the light shielding mask 140 is not attached to the mask accommodation portion 134 provided at the upper end of the opening 135 for a prism, most of the measurement light reflected and condensed by the primary mirror 111 is irradiated to the ATR prism 138 and the contact point P of the sample S. On the other hand, when the light shielding mask 140 is attached to the mask accommodation portion 134, among the measurement light, only the light passed through the slit 144 of the light shielding mask 140 is irradiated to the contact point P.

Figure 3:
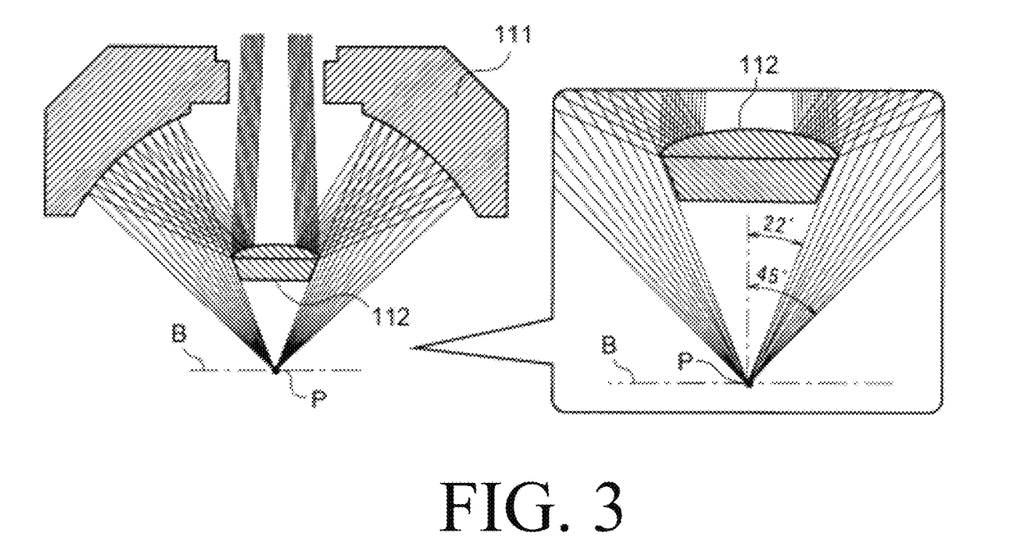
FIG. 3 is a schematic diagram showing an optical path of measurement light in a case in which a light shielding mask is not attached to the objective optical system.
Figure 4:
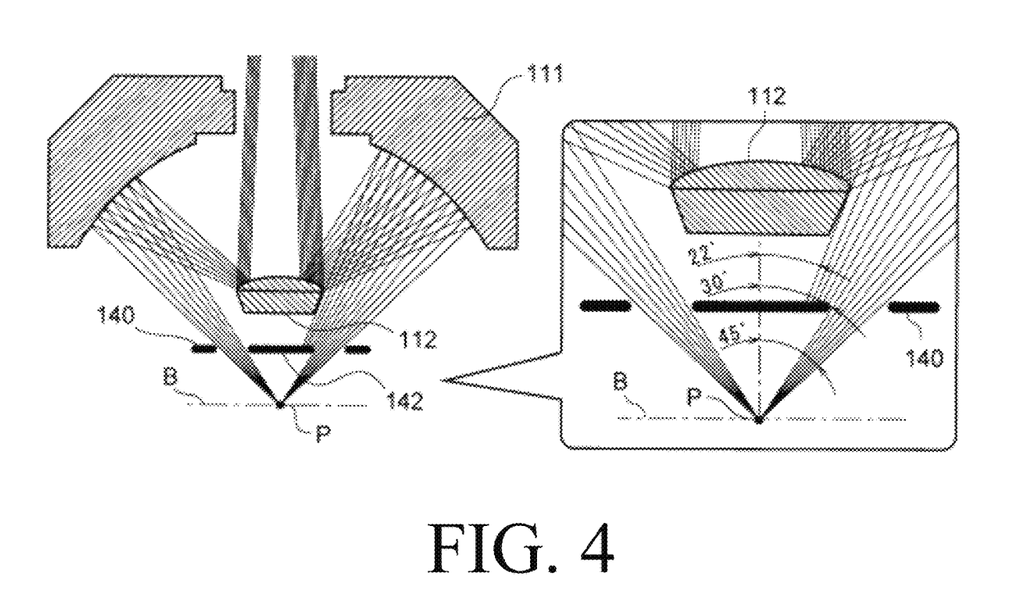
FIG. 4 is a schematic diagram showing an optical path of measurement light in a case in which a light shielding mask is attached to the objective optical system.

The difference in the optical path of the measurement light at this time will be described with the example shown in FIGS. 3 and 4. In the case in which the light shielding mask 140 is not attached to the slide plate 130, as shown in FIG. 3, most of the light beam of the measurement light reflected and condensed by the primary mirror 111 is incident on the contact point P. As a result, the incident angle of the measurement light with respect to the boundary surface B between the sample S and the ATR prism 138 is, for example, 22° to 45°. On the other hand, when the light shielding mask 140 is attached to the slide plate 130, as shown in FIG. 4, among the light beams of the measurement light, the light in the range of the incident angle of 22° to 30° is shielded by the light shielding portion 142 of the light shielding mask 140 and is not incident on the contact point P. That is, the incident angle of the measurement light with respect to the boundary surface B is limited to 30° to 45°.

Figure 5:
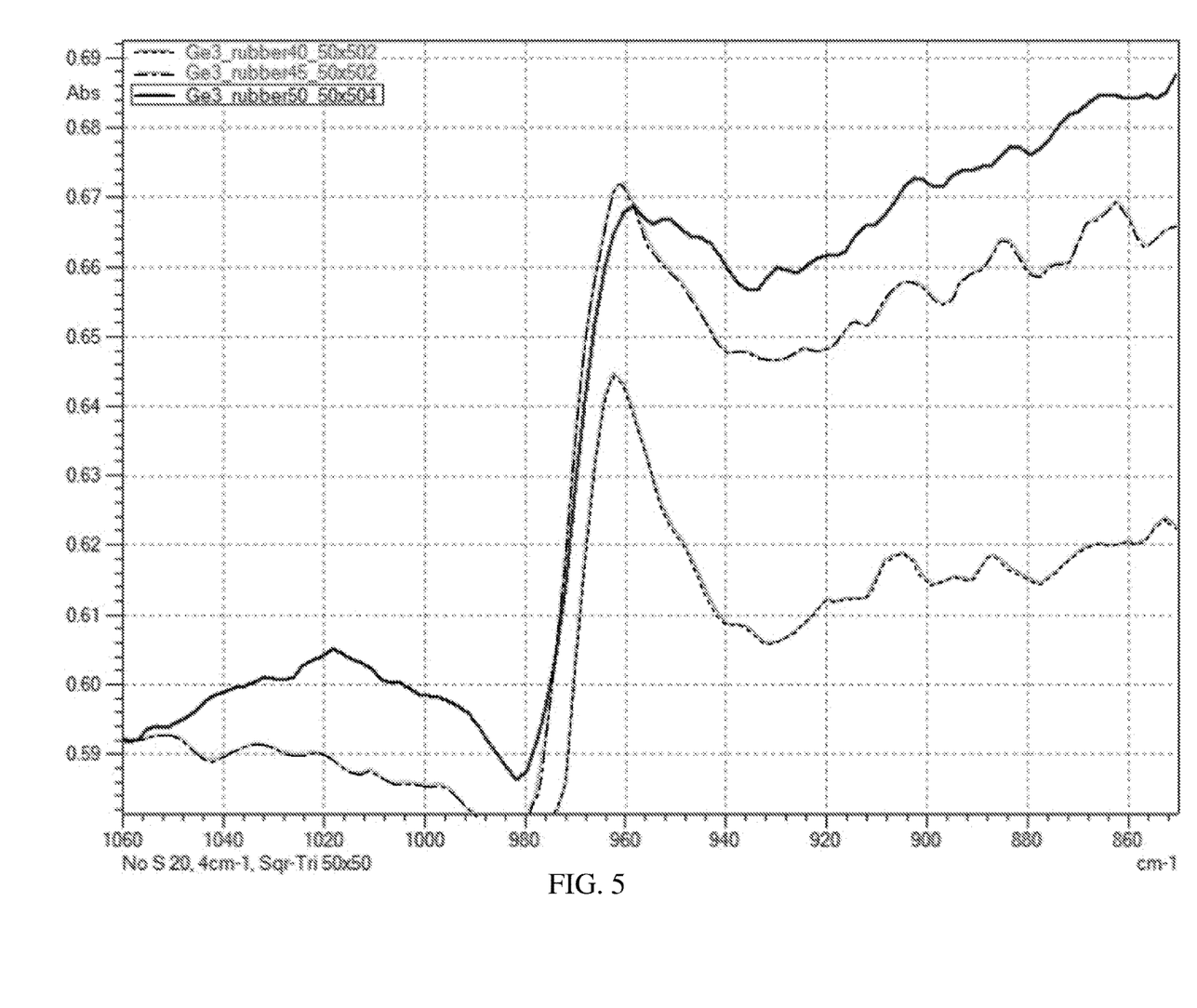
FIG. 5 is a graph showing one example of an absorption spectrum obtained in a state in which a light shielding mask is not attached to the objective optical system.
Figure 6:
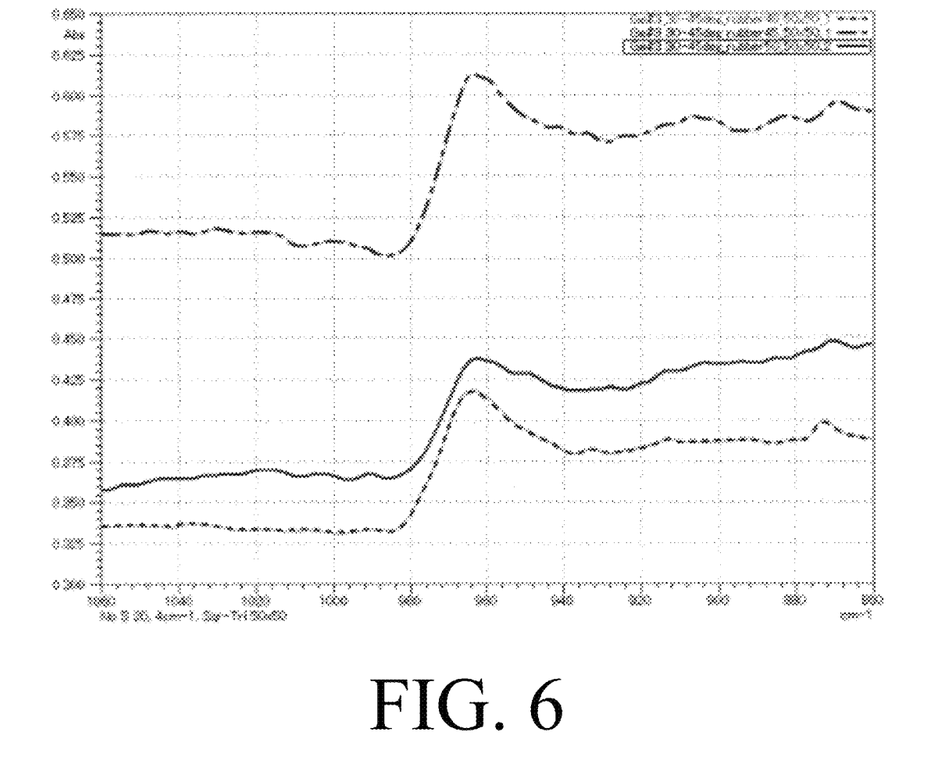
FIG. 6 is a graph showing one example of an absorption spectrum obtained in a state in which a light shielding mask is attached to the objective optical system.

The measurement light incident on the contact point P slightly penetrates the surface of the sample S and then is reflected. The reflected infrared light enters the infrared microscope through the primary mirror 111 and the secondary mirror 112 and is detected by a detection optical system provided in the infrared microscope. An example of the measurement results obtained at this time is shown in FIG. 5 and FIG. 6. These are measurement results by an ATR method using nitrile rubbers (NBR) having different carbon black contents of three kinds (40, 45, 50 wt %), which have a comparatively high content of carbon black, as samples. FIG. 5 shows measurement results in a state in which the light shielding mask 140 is not attached to the slide plate 130 (that is, in a state in which the incident angle is 22° to 45°), and FIG. 6 shows measurement results in a state in which the light shielding mask is attached to the slide plate 130 (in a state in which the incident angle is 30° to 45°). From these figures, in the ATR measurement of the same sample, it is apparent that in the state in which the light shielding mask 140 is attached, even when the carbon black content is high, the peak is not distorted to the differential shape, and the correct peak wave number (996 cm$^{-1}$) in which the shift to the low wave number is eliminated is shown. In other words, it is understood that the effect of anomalous dispersion due to the incident light near the critical angle was relaxed by shielding the light of a small incident angle.

Figure 7A:
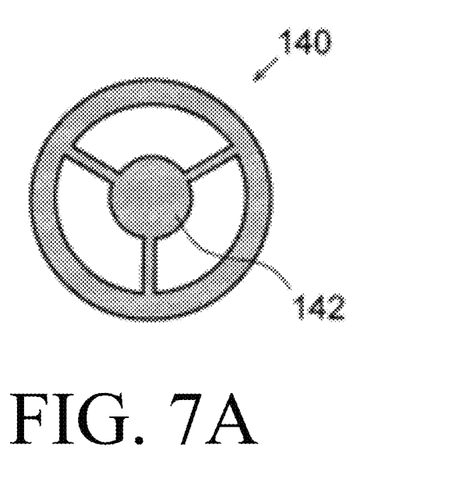
FIG. 7A shows a light shielding mask with a light shielding portion of a small diameter.
Figure 7B:
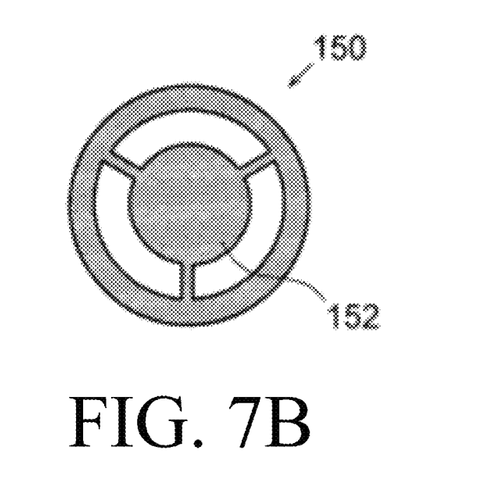
FIG. 7B shows a light shielding mask with a light shielding portion of a large diameter.

In the above description, the configuration in which the incident angle range of the measurement light can be switched between two types depending on the presence or absence of the light shielding mask 140 has been described as an example, but the present invention is not limited to this. For example, a plurality of light shielding masks may be selectively used. Specifically, for example, by preparing two types of light shielding masks 140 and 150 different in the size of the light shielding portions 142 and 152 as shown in FIGS. 7A and 7B and selecting either one of the light shielding masks 140 and 150 or not using both the light shielding mask 140, 150, it is possible to achieve a configuration capable of performing measurements of three types of incident angle ranges. Even in the case of using a plurality of light shielding masks as described above, as described above, it may be configured such that without fixing the light shielding mask to the slide plate, only the light shielding mask may be exchanged according to the required incident angle. Alternatively, it may be configured such that the light shielding mask is fixed to the slide plate and the sliding plate can be exchanged according to the required incident angle.

Figure 8A:
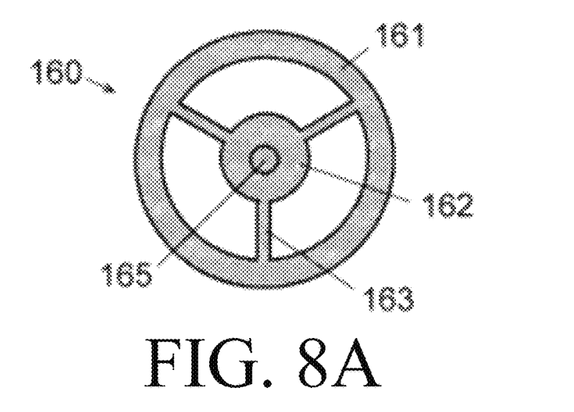
FIG. 8A is a plan view of a support.
Figure 8C:
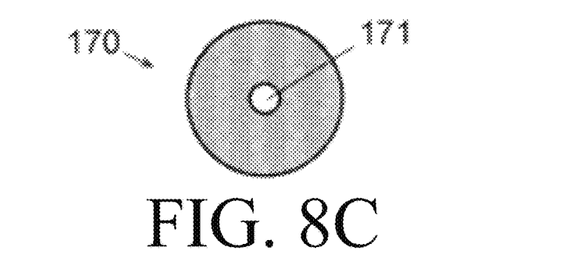
FIG. 8C is a plan view of a light shielding mask.
Figure 8D:
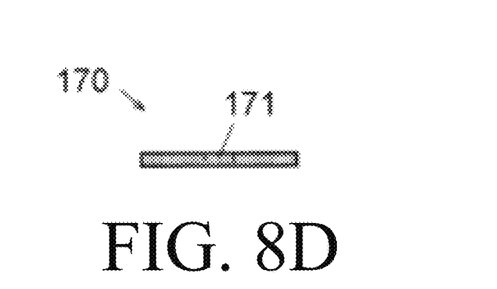
FIG. 8D is a front view thereof.
Figure 8E:
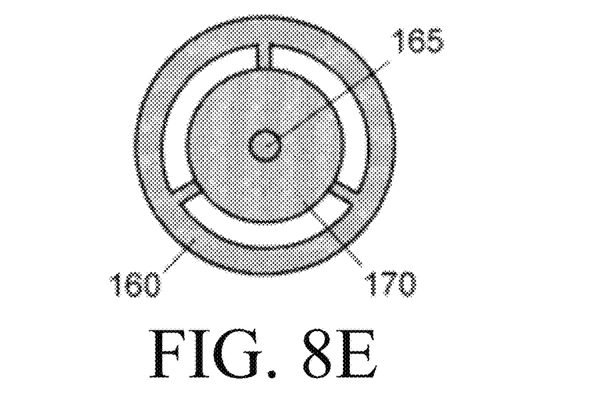
FIG. 8E is a plan view showing a state in which a light shielding mask is placed on the support.
Figure 8F:
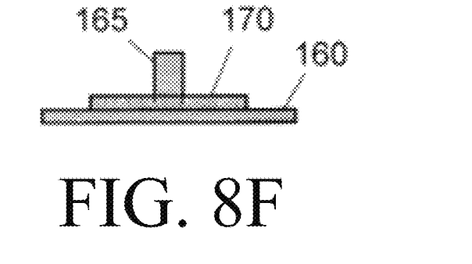
FIG. 8F is a front view thereof.

Alternatively, it may be configured such that as shown in FIGS. 8A and 8B, a support 160 composed of an annular frame part 161, a circular central part 162, and connecting parts 163 connecting the annular frame part 161 and the circular central part 162 is fixed to the mask accommodation portion 134 of the slide plate 130 with adhesive, etc., and a light shielding mask 170 made of a circular light shielding plate having a diameter which is smaller than the inner diameter of the frame part 161 and larger than the outer diameter of the central part 162, as shown in FIGS. 8C and 8D, is placed on the upper surface of the support 160. FIGS. 8E and 8F show a state in which the light shielding mask 170 is placed on the support 160. According to such a configuration, the incident angle of the measurement light to the boundary surface B can be changed between the state in which the light shielding mask 170 is placed on the support 160 and the state in which the light shielding mask 170 is not placed. Alternatively, it may be configured such that a plurality of light shielding masks 170 having different diameters are prepared so that the incident angle can be changed in multiple steps by replacing the light shielding mask 170 placed on the support 160 as required. It is preferable that a protrusion 165 protruding upward be provided at the center of the support 160 and a through-hole 171 to be engaged with the protrusion 165 be provided at the center of the light shielding mask 170. With this, it is possible to easily position the light shielding mask 170 at the center of the support 160.

Embodiment 2

Figure 9:
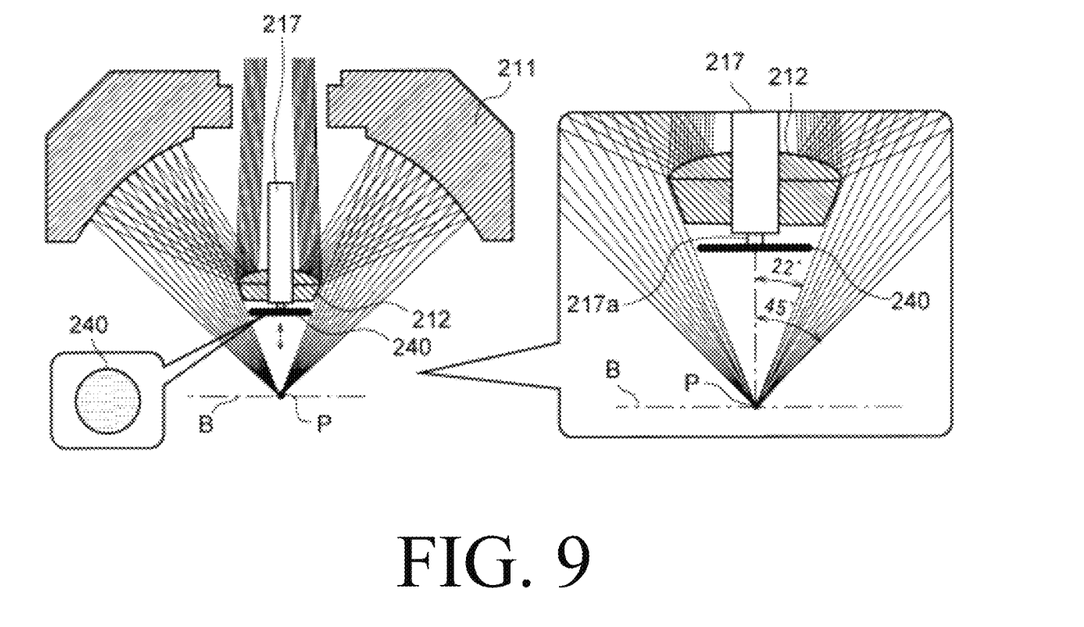
FIG. 9 is a schematic diagram showing a state in which a light shielding mask is retracted from an optical path of measurement light in an objective optical system according to a second embodiment of the present invention.
Figure 10:
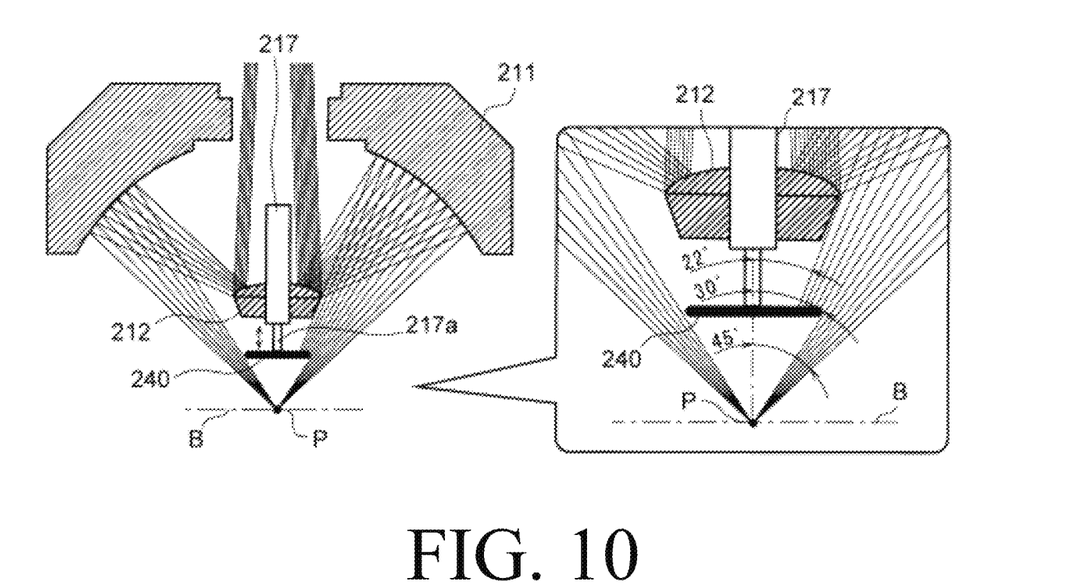
FIG. 10 is a schematic diagram showing a state in which a light shielding mask is inserted on an optical path of measurement light in the aforementioned embodiment.

FIGS. 9 and 10 each are a vertical cross-sectional view of an objective optical system according to a second embodiment of the present invention. Constituent elements that are the same as or correspond to those shown in FIGS. 1 to 4 are denoted by the same reference numerals in the last two digits, and description thereof will be omitted as appropriate. In these figures, components other than the primary mirror 211, the secondary mirror 212, the light shielding mask 240, and the actuator 217 (described later) are not shown. For omitted components, conventionally known components can be adopted as components of an objective optical system for an ATR measurement.

In the objective optical system, the light shielding mask 240 is arranged below the secondary mirror 212, and the incident angle of the measurement light to the boundary surface B can be changed by vertically moving the light shielding mask 240. Specifically, an actuator 217 for driving the light shielding mask 240 is attached so as to penetrate the center of the secondary mirror 212, and a light shielding mask 240 made of a circular light shielding plate is attached to the lower end of a drive shaft 217a provided at the lower portion of the actuator 217. Note that the area surrounded by the square frame in the lower left in FIG. 9 shows a state in which the light shielding mask 240 is viewed from below. The actuator 217 is controlled by a control unit (not shown). When a user inputs a desired minimum incident angle to this control unit, the drive shaft 217a is driven upward and downward, so that the light shielding mask 240 is disposed at a position corresponding to the minimum incident angle.

For example, in the example of FIG. 9, when the light shielding mask 240 is moved upward to retract from the optical path of the measurement light, the incident angle of the measurement light becomes 22° to 45°. In the example of FIG. 10, when the light shielding mask 240 is moved downward so as to be positioned in the optical path of the measurement light, the incident angle of the measurement light is limited to 30° to 45°. In this configuration, by continuously changing the vertical position of the light shielding mask 240, it is possible to arbitrarily adjust the minimum incident angle of the measurement light within a predetermined range.

Embodiment 3

Figure 11:
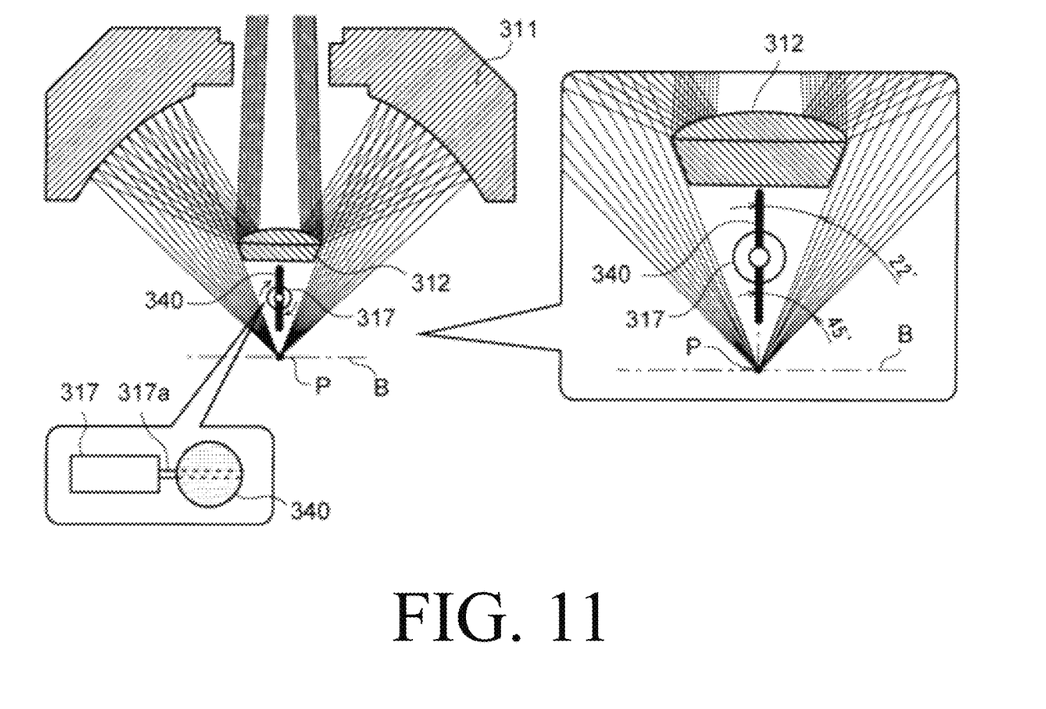
FIG. 11 is a schematic diagram showing a state in which a light shielding mask is retracted from an optical path of measurement light in a third embodiment of the present invention.
Figure 12:
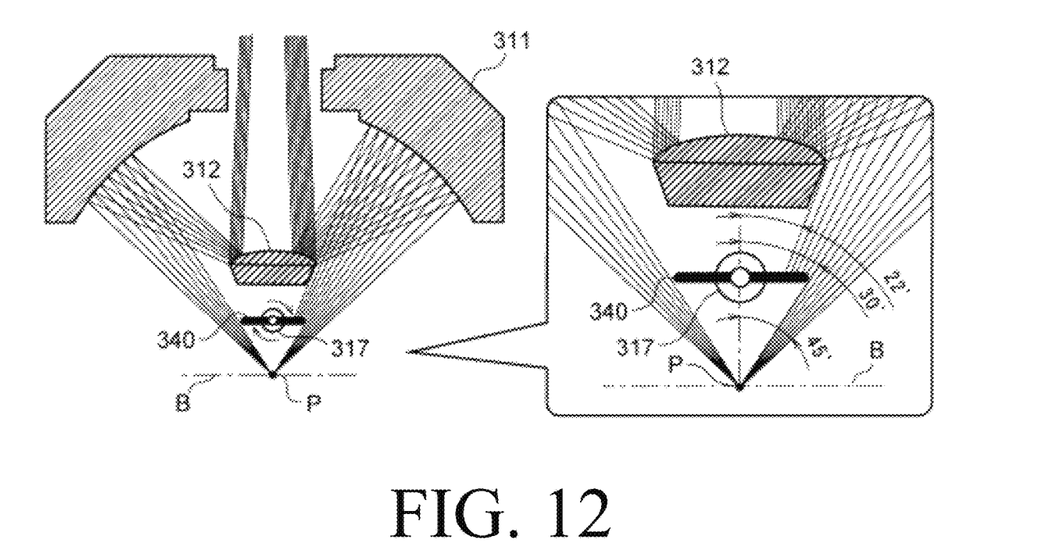
FIG. 12 is a schematic diagram showing a state in which a light shielding mask is inserted on an optical path of measurement light in the aforementioned embodiment.

FIGS. 11 and 12 are vertical cross-sectional views of an objective optical system according to a third embodiment of the present invention. Constituent elements that are the same as or correspond to those shown in FIGS. 1 to 4 are denoted by the same reference numerals in the last two digits, and description thereof will be omitted as appropriate. In these figures, components other than the primary mirror 311, the secondary mirror 312, the light shielding mask 340, and the actuator 317 are not shown. For omitted components, conventionally known components can be adopted as components of the objective optical system for the ATR measurement.

In the objective optical system, the light shielding mask 340 is arranged below the secondary mirror 312, and the incident angle of the measurement light to the boundary surface B can be changed by rotating the light shielding mask 340 about the axis extending in parallel to the light shielding mask 340 and in the horizontal direction. Specifically, the light shielding mask 340 composed of a circular light shielding plate is arranged immediately below the secondary mirror 312 and the actuator 317 for driving the light shielding mask 340 is arranged behind the light shielding mask 340 with the rotation shaft 317a of the light shielding mask 340 facing forward in FIG. 11. The rotation shaft 317a is fixed to the light shielding mask 340 in a state of penetrating the light shielding mask 340 in the diameter direction. Note that the area surrounded by the square frame in the lower left in FIG. 11 shows a state in which the light shielding mask 340 and the actuator 317 are viewed from below. The actuator 317 is controlled by a control unit (not shown). When a user inputs a desired minimum incident angle to this control unit, the rotation shaft 317a is rotatably driven, so that the light shielding mask 340 stops at an angle corresponding to the minimum incident angle.

For example, in the example of FIG. 11, when the light shielding mask 340 is set to a state perpendicular to the boundary surface B, the light shielding mask 340 is retracted from the optical path of the measurement light, so that the incident angle of the measurement light changes from 22° to 45°. Further, in the example of FIG. 12, when the light shielding mask 340 is set to a state parallel to the boundary surface B, the light shielding mask 340 is inserted to the optical path of the measurement light, so that the incident angle of the measurement light is limited to 30° to 45°. In this configuration, by continuously changing the angle of the light shielding mask 340, it is possible to arbitrarily adjust the minimum incident angle of the measurement light within a predetermined range.

DESCRIPTION OF REFERENCE SYMBOLS

110: Cassegrain mirror accommodation portion
111, 211, 311, 511, 611, 711: primary mirror
112, 212, 312, 512, 612, 712: secondary mirror
113, 513, 613, 713: upper opening
114: lower opening
115, 715: baffle
116, 616, 716: mounting portion
120: prism accommodation portion
121: plate accommodation portion
130: slide plate
131: main body portion
134: mask accommodation portion
135: opening for a prism
136 . . . opening for visual observation
137, 537: prism holder
138, 438, 538, 638, 738: ATR prism
140, 150, 170, 240, 340: light shielding mask
141: frame part
142, 152: light shielding portion
143: connecting portion
144: slit
217, 317: actuator
580: sample stage
B: boundary surface
P: contact point
S: sample

The invention claimed is:

1. An objective optical system used for sample surface analysis by an attenuated total reflectance method by being attached to an infrared microscope, comprising:
    a convex secondary mirror configured to reflect measurement light irradiated from the infrared microscope;
    a concave primary mirror configured to reflect the measurement light reflected by the secondary mirror;
    a prism to which the measurement light reflected by the primary mirror is irradiated;
    a housing which accommodates the primary mirror and the secondary mirror;
    a prism holder which holds the prism;
    a slide plate selectively held at a lower portion of the housing, the slide plate being horizontally movable and thereby attachable to and detachable from the housing by the horizontal movement, the slide plate having an opening for accommodating the prism holder and prism; and
    a light shielding mask that is attached to the upper part of the opening for accommodating the prism holder and prism, the light shielding mask being configured to shield a part of a light beam of the measurement light incident on the prism.

2. The objective optical system according to claim 1, further comprising:
    an opening for visual observation which is a through hole provided in the slide plate,
    wherein the slide plate is configured to move horizontally with respect to the housing and thereby switch the objective optical system between a first state in which the prism is disposed on the optical path of the measurement light and a second state in which the opening for visual observation is disposed on the optical path.

3. The objective optical system according to claim 1, further comprising:
an additional slide plate selectively held at a lower portion of the housing, the additional slide plate being horizontally movable and thereby attachable to and detachable from the housing by the horizontal movement, the additional slide plate having an opening for accommodating the prism holder and prism; and
an additional light shielding mask that is attachable to and detachable from the additional slide plate at the upper part of the opening for accommodating the prism holder and prism, the additional light shielding mask being configured to shield a part of a light beam of the measurement light incident on the prism.

4. An objective optical system used for sample surface analysis by an attenuated total reflectance method by being attached to an infrared microscope, comprising:
a convex secondary mirror configured to reflect measurement light irradiated from the infrared microscope;
a concave primary mirror configured to reflect the measurement light reflected by the secondary mirror;
a prism to which the measurement light reflected by the primary mirror is irradiated, and
a light shielding mask configured to shield a part of a light beam of the measurement light on an optical path of the measurement light between the primary mirror and the prism,
wherein the primary mirror is provided with an opening for introducing measurement light and arranged with the concave surface facing downward,
wherein the secondary mirror is arranged below the primary mirror with the convex surface facing upward,
wherein the primary mirror and the secondary mirror are positioned such that the light beam of the measurement light received from above the primary mirror through the opening is reflected by the convex surface of the secondary mirror and the reflected light is reflected again at the concave surface of the primary mirror to be condensed at a single point below the secondary mirror,
wherein the prism is arranged below the secondary mirror,
wherein the light shielding mask is arranged horizontally between the secondary mirror and the prism, and
wherein the light shielding mask is configured to be movable upward and downward so as to approach the prism and move away from the prism.

5. An objective optical system used for sample surface analysis by an attenuated total reflectance method by being attached to an infrared microscope, comprising:
a convex secondary mirror configured to reflect measurement light irradiated from the infrared microscope;
a concave primary mirror configured to reflect the measurement light reflected by the secondary mirror;
a prism to which the measurement light reflected by the primary mirror is irradiated, and
a light shielding mask having a circular shape configured to shield a part of a light beam of the measurement light on an optical path of the measurement light between the primary mirror and the prism,
wherein the primary mirror is provided with an opening for introducing measurement light and arranged with the concave surface facing downward,
wherein the secondary mirror is arranged below the primary mirror with the convex surface facing upward,
wherein the primary mirror and the secondary mirror are positioned such that the light beam of the measurement light received from above the primary mirror through the opening is reflected by the convex surface of the secondary mirror and the reflected light is reflected again by the concave surface of the primary mirror to be condensed on a single point below the secondary mirror,
wherein the prism is arranged below the secondary mirror,
wherein the light shielding mask is arranged between the secondary mirror and the prism and the light shielding mask is without an opening, and
wherein the light shielding mask is configured to be rotatable about a horizontal axis extending parallel to the light shielding mask and passing through the center of the light shielding mask.

* * * * *